(12) United States Patent
Szasz

(10) Patent No.: US 8,642,264 B2
(45) Date of Patent: Feb. 4, 2014

(54) METHOD OF QUANTIFYING TARGET AND REFERENCE NUCLEIC ACID

(75) Inventor: Nora Szasz, Weston, MA (US)

(73) Assignee: Zoragen Biotechnologies LLP (GB)

( * ) Notice: Subject to any disclaimer, the term of this patent is extended or adjusted under 35 U.S.C. 154(b) by 954 days.

(21) Appl. No.: 11/909,557

(22) PCT Filed: Mar. 23, 2006

(86) PCT No.: PCT/US2006/010699
§ 371 (c)(1),
(2), (4) Date: Jun. 11, 2010

(87) PCT Pub. No.: WO2006/102569
PCT Pub. Date: Sep. 28, 2006

(65) Prior Publication Data
US 2010/0267015 A1    Oct. 21, 2010

Related U.S. Application Data

(60) Provisional application No. 60/664,853, filed on Mar. 24, 2005.

(51) Int. Cl.
*C12Q 1/68*      (2006.01)
*C12P 19/34*     (2006.01)
*C07H 21/04*     (2006.01)

(52) U.S. Cl.
USPC ...... 435/6.12; 435/6.14; 435/91.2; 536/24.33

(58) Field of Classification Search
None
See application file for complete search history.

(56) References Cited

U.S. PATENT DOCUMENTS

| 5,543,507 A |   | 8/1996 | Cook |  |
|---|---|---|---|---|
| 5,589,339 A | * | 12/1996 | Hampson et al. | 506/17 |
| 5,591,575 A |   | 1/1997 | Hampson |  |
| 5,627,054 A |   | 5/1997 | Gillespie |  |
| 6,287,778 B1 | * | 9/2001 | Huang et al. | 506/4 |
| 2002/0142300 A1 | * | 10/2002 | Bernard et al. | 435/6 |

FOREIGN PATENT DOCUMENTS

| WO | 2004046378 | 6/2004 |
|---|---|---|
| WO | 2005072133 | 8/2005 |

OTHER PUBLICATIONS

Metzler et al. British Journal of Haematology (2004) 124: 47-54.*
Parker, W. B. et al., "Interaction of 2-Halogenated dATP Analogs (F, Cl, and Br) with Human DNA Polymerases, DNA Primase, and Ribonucleotude Reductase", Molecular Pharmacology, Oct. 1988, vol. 34, No. 4, pp. 485-491.
International Search Report for PCT/US06/10699, mailed Mar. 21, 2008.
EPO Search Report, MG40865p.EPP, Dated Dec. 22, 2009.

* cited by examiner

*Primary Examiner* — Angela M Bertagna
(74) *Attorney, Agent, or Firm* — Boulware & Valoir

(57) ABSTRACT

The invention provides methods for the detection of the amount of a nucleic acid in a sample. The described methods exploit the ability to disrupt and redirect a PCR direction, and the ability to physically pair nucleic acid molecules in a sample that have a reference sequence with nucleic acid molecules in the sample that have a target sequence. The redirection of the PCR reaction enables partial amplification as a preparatory step to other techniques within the same tube. The pairing can result in the presence of unpaired target or reference sequence indicating a difference in the amount of the target sequence versus the reference sequence. The methods are broadly applicable for the determination of differences in the amount of nucleic acids in diagnostic and research applications.

15 Claims, 4 Drawing Sheets

METHOD OF QUANTIFYING TARGET AND REFERENCE NUCLEIC ACID

This application is a National Stage of International Application PCT/US2006/010699, filed Mar. 23, 2006, published Sep. 28, 2006, which claims the priority of U.S. Provisional Application No. 60/664,853, filed Mar. 24, 2005.

FIELD OF INVENTION

This invention relates to the field of nucleic acid detection.

BACKGROUND OF THE INVENTION

The detection of small differences in nucleic acid content is an important task within the field of molecular diagnostics.

The most common method used to detect small quantities of nucleic acids is by using PCR or RT-PCR. These methods perform exceptionally well in determining whether a to sequence of interest is present in a given sample or not, but in order to determine if there is a difference between the concentration of two sequences, approximately a 2-fold difference is needed.

Quantitative analysis of nucleic acid is used for example, in quality control, gene expression analysis, medical monitoring and diagnosis. Methods are described herein that significantly improve the accuracy of these measurements, opening up new possibilities within science and medicine.

SUMMARY OF THE INVENTION

In one aspect, the invention provides improved methods for quantitating the amount of a nucleic acid sequence in a nucleic acid sample. The claimed methods can permit the accurate detection of the amount of a nucleic acid having a given sequence in a sample, including accurate determination of differences of less than two-fold.

In one aspect, the methods rely upon a method of misbalancing a PCR reaction. When the reaction is misbalanced in this manner, an asymmetry is created between template and complementary strands that permits subsequent differentiation between desired and undesired products in the reaction, which permits sensitive detection of even small differences in the amounts of nucleic acid sequences in nucleic acid samples.

In one embodiment, then, a method of misbalancing a PCR reaction is provided that comprises the steps of: a) generating products in a PCR reaction that include the original nucleic acid sequence of interest (template), its complement nucleic acid sequence, and the corresponding first and second PCR primers; and b) adding an excess of a nucleic acid disruption sequence that is complementary to one or the other of the first and second PCR primers. In the discussion that follows, the disruption sequence is complementary to the first primer. When the disruption sequence is allowed to hybridize in the next annealing cycle, it predominantly forms disruption sequence pairs by annealing to the first primer and to one or the other of the original (template) sequence or its complement, but not both (depending upon which of these two strands has the complement of the disruption sequence). Products generated by subsequent extension are misbalanced such that one strand, either template or its complement, is produced, but not both. That is, upon extension after hybridization of the disruption sequence(s), there is produced predominantly either: a) a double stranded original (template) sequence with a break in one of the strands and a single stranded complement sequence, OR b) a double stranded complement sequence with a break in one of the strands and a single stranded original (template) sequence. The identity of which product is produced in single or double-stranded form is determined by which of the two PCR primers is complementary to the disruption sequence. Detection of the single stranded product permits sensitive measurement of the original amounts of a target sequence.

In another aspect, a method is provided for blocking future PCR-based amplification in a reaction mixture by locking double stranded DNA through cross-linking. The cross-linking prevents the amplification and thereby the detection of DNA that was double-stranded at the time of cross-linking. This blockage of amplification can permit more sensitive detection of the products that were not cross-linked. The cross-linking can be accomplished by, e.g., UV or chemical treatment.

In another aspect, a method is provided for determining the amount of a target nucleic acid relative to the amount of a reference nucleic acid in a nucleic acid sample. The method comprises performing PCR on a combined mixture of the reference and target nucleic acid, along with the forward and reverse PCR primers for both the reference and target nucleic acids. The reverse PCR primer for the reference contains a tail sequence that is identical to a sequence found on the target nucleic acid. Following a given number of cycles of PCR, the symmetry of the reaction is disrupted by adding excess amounts of two nucleic acid disruption sequences and letting them hybridize to the single stranded PCR products. The first disruption sequence is complementary to the target probe's reverse primer, and the second disruption sequence is complementary to the reference probe's reverse primer but not including the tail region that is identical to a sequence found on the target nucleic acid.

Following disruption, remaining single stranded target or reference is detected, such that the amount of target in the original sample is determined relative to the reference.

DESCRIPTION OF THE DRAWINGS

FIG. 3 shows a schematic of a single tube relative amplification technique that can detect much smaller differences in nucleic acid content than previously thought possible. Step 1 shows the starting materials: two genomic DNA sequences one would like to compare, and respective forward and reverse PCR primers, with the reverse primer of the reference sequence having a "tail" with partial B sequence. After performing several cycles of PCR, the products seen in step 2 will be produced. If after this step one adds excess C and F primers to the reactions, these can hybridize to the reverse primers and the complement sequences, leaving the template strands untouched by either the newly added C and F primers, or the previously added reverse primers. The single stranded reference and target template can then hybridize to each other and form a pair. Any unpaired reference or target template will remain single stranded. Step 4 shows what happens if the double stranded DNA is cross-linked. Cross-linking only has to happen on the C/C' and pB/pB' sequences. If the cross-linking has taken place permanently or semi-permanently, direct PCR can be performed using primers that span a cross-linking site to detect only the single stranded template (ABC as shown).

Figure 3:
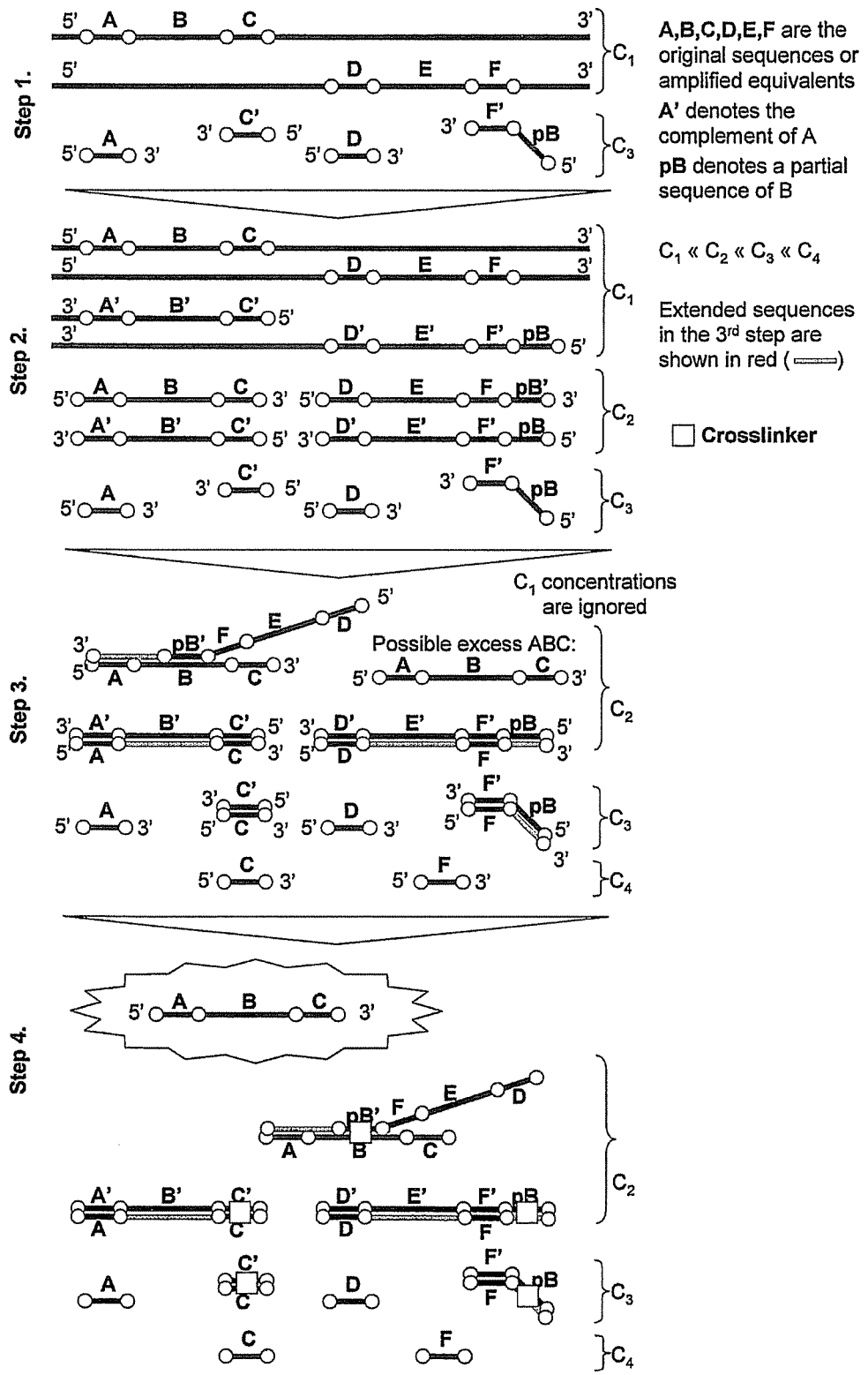
Figure 4:
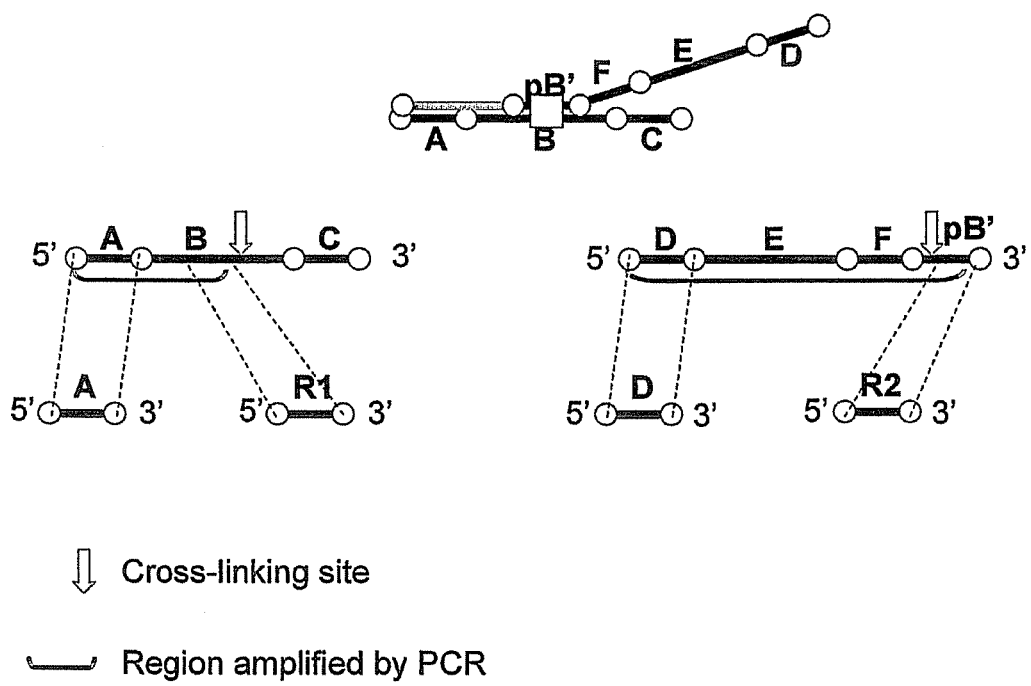

FIG. 4 shows a schematic of an embodiment where the cross-linking of the double stranded template pairs is followed by the detection of the single stranded templates using PCR. The figure shows a possible selection of PCR primers for further analysis, where forward primers A and D were already found in the final sample as seen in Step 4 of FIG. 3, and R1 and R2 where added later. As shown, the primers will only amplify the single stranded templates and will not be able to amplify the cross-linked double stranded template shown on top.

DETAILED DESCRIPTION OF THE INVENTION

Definitions

As used herein, a "polynucleotide" or "nucleic acid" refers to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. The term "polynucleotide" includes, without limitation, single- and double-stranded polynucleotide. The term "polynucleotide" as it is employed herein embraces chemically, enzymatically or metabolically modified forms of polynucleotide comprising, e.g., DNA, RNA, PNA, combinations of these and/or polymers containing one or more nucleotide analogs. A "nucleotide analog", as used herein, refers to a nucleotide in which the pentose sugar and/or one or more of the phosphate esters is replaced with its respective analog. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., including any associated counterions, if present. Also included within the definition of "nucleotide analog" are nucleobase monomers which can be polymerized into polynucleotide analogs in which the DNA/RNA phosphate ester and/or sugar phosphate ester backbone is replaced with a different type of linkage. Further included within "nucleotide analogs" are nucleotides in which the nucleobase moiety is non-conventional, i.e., differs from one of G, A, T, U or C. For example, halogenated nucleotides such as bromodeoxyuridine can be employed. Generally a non-conventional nucleobase will have the capacity to form hydrogen to bonds with at least one nucleobase moiety present on an adjacent counter-directional polynucleotide strand or provide a non-interacting, non-interfering base.

"Polynucleotide" also embraces a short polynucleotide, often referred to as an oligonucleotide (e.g., a primer or a probe). A polynucleotide has a "5'-terminus" and a "3'-terminus" because polynucleotide phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus. As used herein, a polynucleotide sequence, even if internal to a larger polynucleotide (e.g., a sequence region within a polynucleotide), also can be said to have 5'- and 3'-ends.

As used herein, the term "chemically modified," when used in the context of a nucleotide, refers to a nucleotide having a difference in at least one chemical bond relative to a standard ATP, CTP, GTP, UTP, dATP, dCTP, dGTP or dTTP nucleotide. The "chemical modification" does not refer to the modification occurring when a nucleotide is incorporated into a polynucleotide by 5' to 3' phosphodiester linkage.

As used herein, the term "hybridization" is used in reference to the physical interaction of complementary (including partially complementary) polynucleotide strands by the formation of hydrogen bonds between complementary nucleotides when the strands are arranged antiparallel to each other. Hybridization and the strength of hybridization (i.e., the strength of the association between polynucleotide strands) is impacted by many factors well known in the art including the degree of complementarity between the polynucleotides, and the stringency of the conditions involved, which is affected by such conditions as the concentration of salts, the presence of other components (e.g., the presence or absence of polyethylene glycol), the molarity of the hybridizing strands and the G+C content of the polynucleotide strands, all of which results in a characteristic melting temperature ($T_m$) of the formed hybrid.

As used herein, when one polynucleotide is said to "hybridize" to another polynucleotide, it means that the two polynucleotides form a hydrogen-bonded antiparallel hybrid under high stringency conditions. Hybridization requires partial or complete sequence complementarity between the polynucleotides that hybridize. When one polynucleotide is said to not hybridize to another polynucleotide, it means that there is insufficient sequence complementarity between the two polynucleotides to form a hydrogen-bonded hybrid, or that no hybrid forms between the two polynucleotides under high stringency conditions. As used herein, "specific hybridization" refers to the binding, duplexing, or hybrization of a nucleic acid molecule only to a target nucleic acid sequence and not to other non-target nucleic acid molecules in a mixture of both target and non-target nucleic acid sequence.

As used herein, the terms "low stringency," "medium stringency," "high stringency," or "very high stringency conditions" describe conditions for nucleic acid hybridization and washing. Guidance for performing hybridization reactions can be found in Current Protocols in Molecular Biology, John Wiley & Sons, N.Y. (1989), 6.3.1-6.3.6, which is incorporated herein by reference in its entirety. Aqueous and non-aqueous methods are described in that reference and either can be used. Specific hybridization conditions referred to herein are as follows: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5M sodium phosphate, 7% SDS at 65° C., followed by one or more washes at 0.2×SSC, 1% SDS at 65° C.

As used herein, a polynucleotide "isolated" from a sample is a naturally occurring polynucleotide sequence within that sample which has been removed from its normal cellular or non-cellular environment. Thus, an "isolated" polynucleotide that was in a normal cellular environment may be in a cell-free solution or be placed in a different cellular environment. Similarly, an "isolated" polynucleotide that was in a normal non-cellular environment may be in a different cell-free solution or be placed in a cellular environment.

As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

As used herein in the context of a sample, a sample that is obtained "at least partially" from a given source comprises at least one sample component obtained from such a source.

"Complementary" sequences, as used herein, refer to sequences in which antiparallel alignment juxtaposes A residues on one strand with T or U residues and G with C residues on the other strand such that A:T, A:U, and G:C hydrogen-bonded base pairs can form. These are the standard "Watson-Crick" base pairs occurring in the vast majority of DNA and RNA hybrids in vivo. As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. "Complementary" sequences can also include, or be formed entirely from, non-Watson-Crick base pairs and/or base pairs formed from non-natural and modified nucleotides, in as far as the above requirements with respect to their ability to hybridize are fulfilled.

The terms "complementary", "fully complementary" and "substantially complementary" herein may be used with respect to the base matching between the sense strand and the antisense strand of a double-stranded nucleic acid hybrid. A "fully complementary" hybrid has every nucleotide on one strand base paired with its juxtaposed counterpart on the opposite strand. In a "substantially complementary" hybrid, the two strands can be fully complementary, or they can include one or more, but preferably not more than 10 mismatched base pairs upon hybridization, while retaining the ability to hybridize under the conditions used in the methods described herein.

A "chromosomal abnormality", as used herein, refers to any deviation in the DNA composition or structure of a chromosome from that composition or structure most prevalent in a given population. This includes, but is not limited to, deletions, mutations, duplications, rearrangements, covalent modifications, uniparental disomy, and altered chromatin structure. The methods described herein are suited for detecting, among others, abnormal chromosome count (e.g. Down, Klinefelter, Patau, Edward, Turner, Triple-X, XYY, etc.) and abnormal sequence count (an abnormality where only a part of a chromosome is present in abnormal quantities).

The term "oligonucleotide" is defined as a molecule comprised of two or more deoxyribonucleotides and/or ribonucleotides, preferably more than three. Its exact size will depend upon many factors which, in turn, depend upon the ultimate function and use of the oligonucleotide. Oligonucleotides for use in the methods described herein are most often 15 to 600 nucleotides in length. The term "primer" as used herein refers to an oligonucleotide, whether occurring naturally as in a purified restriction digest or produced synthetically, which is capable of acting as a point of initiation of template-dependent nucleic acid synthesis. The primer may be either single-stranded or double-stranded and must be sufficiently long to prime the synthesis of the desired extension product in the presence of the chosen polymerase. The exact length of the primer will depend upon many factors, including hybridization and polymerization temperatures, source of primer and the method used. For example, for diagnostic applications, depending on the complexity of the target sequence, the oligonucleotide primer typically contains 15-25 or more nucleotides, although it may contain fewer or more nucleotides. The factors involved in determining the appropriate length of primer are readily known to one of ordinary skill in the art.

As used herein, "an individual" refers to a human subject as well as a non-human subject such as a mammal, an invertebrate, a vertebrate, a rat, a horse, a dog, a cat, a cow, a chicken, a bird, a mouse, a rodent, a primate, a fish, a frog, a deer, a fungus, a yeast, a bacteria, and a virus. The examples herein are not meant to limit the methodology of the present invention to a human subject only, as the instant methodology is also useful in the fields of veterinary medicine, animal sciences, research laboratories and such.

As used herein, "diagnosis" refers to the ability to demonstrate an increased likelihood that an individual has a specific condition or conditions. Diagnosis also refers to the ability to demonstrate an increased likelihood that an individual does not have a specific condition. More particularly "diagnosis" refers to the ability to demonstrate an increased likelihood that an individual has one condition as compared to a second condition. More particularly "diagnosis" refers to a process whereby there is an increased likelihood that an individual is properly characterized as having a condition ("true positive") or is properly characterized as not having a condition ("true negative") while minimizing the likelihood that the individual is improperly characterized with said condition ("false positive") or improperly characterized as not being afflicted with said condition ("false negative").

As used herein, the term "corresponding to" refers to a nucleotide in a first nucleic acid sequence that aligns with a given nucleotide in a reference nucleic acid sequence when the first nucleic acid and reference nucleic acid sequences are aligned. Alignment is performed, for example, by one of skill in the art using software designed for this purpose. As an example of nucleotides that "correspond," the T at position 11 of the sequence 5'-GTATCACTGA TAAAGGAGAA-3' (SEQ ID NO:1) "corresponds to" the T nucleotide at position 27,091 of Gen Bank Accession # GI:1552506 of TCRB, and vice versa. The term "corresponding" also refers, for example, to the relationship between two specific binding partners—that is, one member of a binding partner pair "corresponds to" the other member of such pair.

As used herein, the phrase "close to the amount of reference or target sequence present" when used in reference to probe concentration means that the concentration of the discussed probe or probes is equal within 80% to the concentration of the reference or the target sequence, whichever might be discussed.

As used herein, a "probe" refers to a type of oligonucleotide having or containing a sequence which is complementary to another polynucleotide, e.g., a target polynucleotide or another oligonucleotide. The probes for use in the methods described herein are ideally less than or equal to 600 nucleotides in length, typically between 40-600 nucleotides.

As used herein, the phrase "paired probes" refers to two probes that are physically associated with or bound to each other. Paired probes can be bound to each other by the association of two binding partner moieties as the term is defined herein, including, but not limited to binding via the formation of nucleic acid hybrids, binding via covalent chemical bonds, or binding via protein-protein interactions. The term "paired probes" encompasses not only probes that are paired in a 1:1 relationship, but also probes associated in higher order relationships, e.g., 1:2, 1:3, 1:4, 1:5, 1:6, 1:7, 1:8, etc. (i.e., one molecule of one probe pairing with 2, 3, 4, 5, 6, 7, or 8 molecules, etc. of a second probe), as long as the ratio is known or at least constant for a given set of probes. An "unpaired probe" is a probe (e.g., a first probe) that is not physically associated with or bound to another (e.g., a second) probe. The "pairing" can occur through one or more adapter molecules.

As used herein, the phrases "rendering hybridized probes resistant to detection" and "rendering paired probes resistant to detection" refer to the treatment of hybridized or paired probes such that they are not substantially detected in the nucleic acid detection method employed to detect unpaired probe. By "not substantially detected" is meant that hybridized or paired probes treated to render them resistant to detection contribute less than 10%, and preferably less than 2% of the signal in the nucleic acid detection method employed to detect unpaired probe. The phrase "rendering hybridized probes resistant to detection" is equivalent to the terms "hiding" or "sequestering" when applied to probes. Non-limiting examples of treatments that render hybridized probes resistant to detection include chemical and U.V. cross-linking of probe to target or reference sequence or to another probe, or the physical removal of said hybridized or paired probes.

As used herein, "binding partner" or "binding partner moiety" refers to a member of a specific binding pair. A specific binding pair is a pair of moieties that specifically bind to each other under a given set of conditions; "specific binding" refers to the binding of one member of the pair to the other member of the pair to the substantial exclusion of the binding of other moieties present in that environment.

As used herein, the phrase "conditions that permit a first binding partner moiety to interact with a second binding partner moiety" refers to those environmental conditions that favor the physical and/or chemical interaction of two members of a specific binding pair. Such conditions will vary depending upon the nature of the binding pair interaction, but can be determined by one of skill in the art. Exemplary conditions include hybridizing conditions as described herein or as known in the art, e.g., conditions of high stringency or below, when, for example, the binding partners are complementary nucleic acid sequences. Such conditions also include the substantial absence of competitor sequences, including sequences present in a nucleic acid sample for which the amount of a target sequence is to be determined. Within the methods described herein, the step of placing binding partner moieties or probes comprising them under conditions that permit a first binding partner moiety to interact with a second binding partner moiety can be performed as a separate step, e.g., following contacting probes with sample nucleic acids, or it can occur during such contacting.

As used herein, the term "target nucleic acid" refers to a polynucleotide whose amount is to be determined in a sample, relative to a "reference nucleic acid." A "target nucleic acid" contains a known sequence of at least 20 nucleotides, preferably at least 50 nucleotides, more preferably between 80 to 500 nucleotides but can be longer. A "target nucleic acid" of the invention can be a naturally occurring polynucleotide (i.e., one existing in nature without human intervention), or a recombinant polynucleotide (i.e., one existing only with human intervention), including but not limited to genomic DNA, cDNA, plasmid DNA, total RNA, mRNA, tRNA, rRNA. The target polynucleotide also includes amplified products of itself, for example, as in a polymerase chain reaction. As used herein, a "target polynucleotide" or "target nucleic acid" can contain a modified nucleotide which can include phosphorothioate, phosphite, ring atom modified derivatives, and the like. Target nucleic acid sequence necessarily differs from reference nucleic acid sequence, such that target and reference nucleic acid sequences cannot hybridize to each other under stringent conditions.

As used herein, the term "cross-linking" refers to covalent linkage of one probe to another, following a specific physical interaction between the two probes.

"Homology" or "identity" or "similarity" refer to sequence similarity between two nucleic acid sequences or between two polypeptide sequences. Homology can be determined by comparing a position in each sequence which may be aligned for purposes of comparison. When several positions of a compared sequence are occupied by the same bases or amino acids, then the molecules are homologous at that sequence. A degree of homology between sequences is a function of the number of matching or homologous positions shared by the sequences. An "unrelated" or "non-homologous" sequence shares less than 40% identity, to though preferably less than 25% identity, with another sequence.

As used herein, the term "biological fluid" refers to a liquid taken from a biological source and includes, for example, blood, serum, plasma, sputum, lavage fluid, cerebrospinal fluid, urine, semen, sweat, tears, saliva, and the like.

As used herein, the phrase "resistant to nuclease cleavage" means that a given nucleic probe contains one or more chemical modifications or structural attributes that render it less susceptible to nuclease cleavage than a similar sequence without the modification or structural attribute. Non-limiting examples include changes to the phosphodiester linkages, e.g., the inclusion of a thiol linkage, and the presence of secondary structure, e.g., double-strandedness versus single strandedness over all or part of the probe molecule. By "less susceptible" is meant at least 10% fewer cleavage events relative to non-modified probe under the same nuclease cleavage conditions.

As used herein, the term "aneuploidy" refers to the state of having a chromosome number that is not a multiple of the haploid number for the species. For example, a diploid cell or organism having a total number of chromosomes which is different from (e.g., either greater than or less than) a multiple of two times the haploid number of chromosomes would be aneuploid.

As used herein, "polymerase chain reaction" or "PCR" refers to an in vitro method for amplifying a specific polynucleotide template sequence. The PCR reaction involves a repetitive series of temperature cycles and is typically performed in a volume of 10-100 µl. The reaction mix comprises dNTPs (each of the four deoxynucleotides dATP, dCTP, dGTP, and dTTP), primers, buffers, DNA polymerase e.g., a thermostable DNA polymerase, and polynucleotide template.

One PCR reaction may consist of, for example, 5 to 100 "cycles" of denaturation and synthesis of a polynucleotide molecule.

A "hairpin sequence", as used herein, comprises two self-complementary sequences that may form a double-stranded stem region, separated by a loop sequence. The two regions of the oligonucleotide which comprise the double-stranded stem region are substantially complementary to each other, resulting in self-hybridization. However, the stem can include one or more mismatches, insertions, sideloops, or deletions. The "hairpin sequence", as used to herein, can additionally comprise single-stranded region(s) that extend from the double-stranded stem segment.

DESCRIPTION

Misbalancing a PCR Reaction at a Favorable Time to Allow the Redirection of the Process Although PCR is a commonly accepted methodology in molecular biology, the basic idea behind this methodology has changed very little in the past 20 years. The primary reason for this is that PCR has served the molecular biology community well. It is a tool that can detect extremely low quantities of nucleic acid sequences and it can even provide a rough quantitative analysis. One of the recurring problems with PCR, however, has been around the formation of a number of by-products in the final PCR mixture that make these PCR products unusable in many applications.

Described herein is a method by which the PCR reaction can be selectively unbalanced. As used herein, the term "unbalancing" or "misbalancing" with respect to PCR refers to the use of PCR or a variant of PCR to produce an amplification product containing both single stranded and double stranded nucleic acids, i.e., to create either a single stranded template and a double stranded complement or to create a double stranded template and a single stranded complement. The purpose of this misbalancing is to facilitate differentiation between the template and its complement, thereby permitting downstream reactions with one, but not the other.

Figure 1:
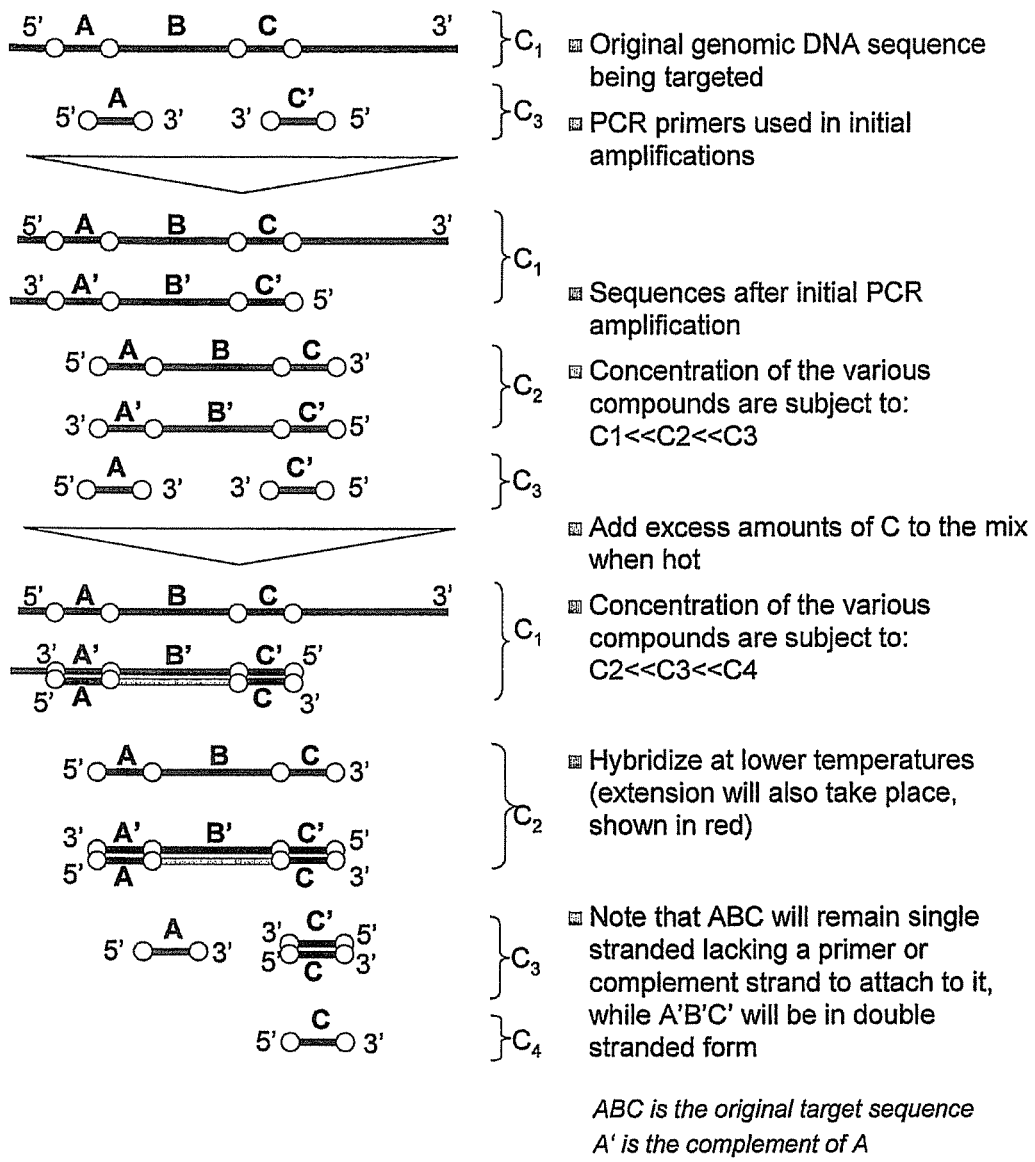
FIG. 1 shows a schematic of controlled disruption of a PCR reaction to create a single stranded template (ABC) and a double stranded complement (C'B'A'). The first step shows the original genomic DNA sequence (a.k.a. template, ABC) and the respective forward and reverse PCR primers (A and C', respectively). In the second step, the products of several PCR cycles are shown. After completion of the desired number of PCR steps, the schematic shows the addition of a disruption sequence (C) complementary to the reverse primer (C') in excess to the PCR primers. When cooled, the excess disruption sequence will bind the reverse primer, and the complement sequences. At the same time, the forward primer will bind the complement and extend, creating a double stranded complement with a break at the junction of B and C. The template (ABC) therefore, will remain single stranded.

After several PCR cycles, a reaction mixture contains an assortment of products. A way to misbalance the reaction at this stage is to introduce an excess of the full or partial complement to the forward or the reverse primers (or potentially, both) The added excess primer is referred to herein as the "disrupt sequence" or "disruption sequence." If this disrupt sequence is allowed to hybridize to the single stranded PCR products, half of the products will become double stranded, while the other half will remain single stranded (FIG. 1). Note that the double stranded complement or template will not be a continuous strand, but rather will exhibit a break in the sequence where the disrupt sequence meets the extension of the original primer that is not complemented by the disrupt sequence.

Therefore, through this simple method of misbalancing the final PCR reaction, the method differentiates between the intended PCR products and their complements.

Figure 2:
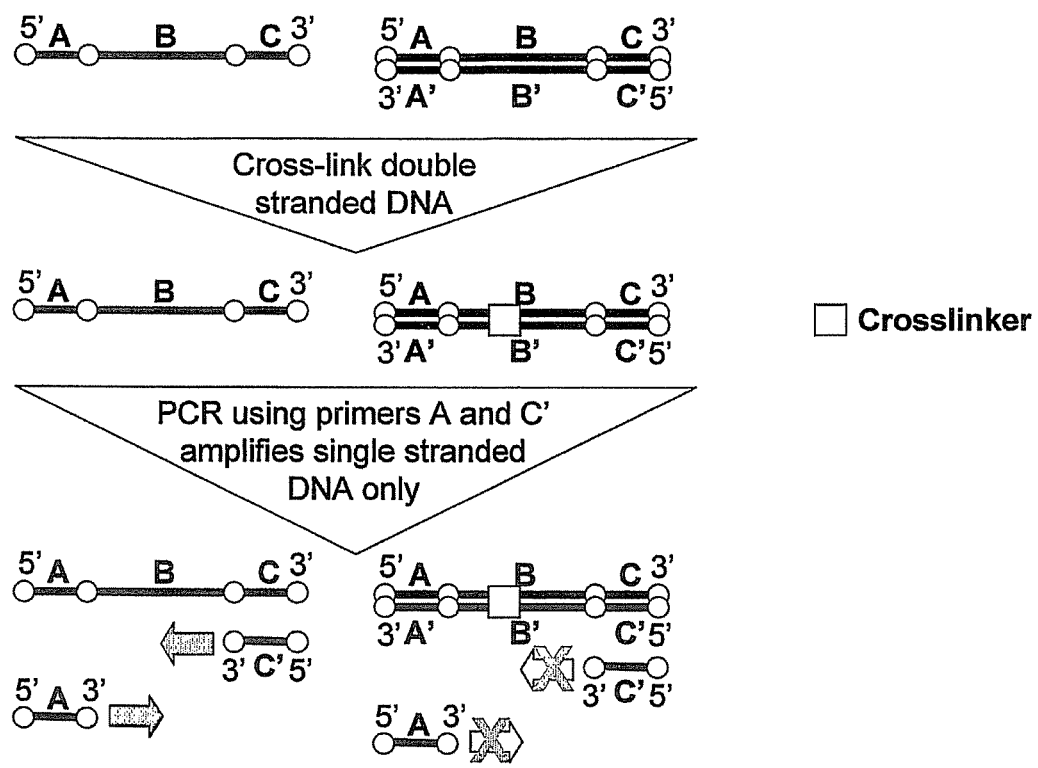
FIG. 2 shows a schematic of how to eliminate double stranded DNA from a subsequent PCR or other detection reaction using cross-linking. Step 1 shows the presence of a sequence in both single stranded and double stranded form. Adding a cross-linking agent binds the double stranded DNA together permanently or semi-permanently, preventing complete dissociation during the high temperature step of the PCR cycle (step 3). This prevents amplification of the double DNA e.g., by PCR, but does not limit the single stranded DNA amplification, selectively.

Knocking Out Nucleic Acids from Future Detection by PCR or Other Methods Requiring Single Stranded DNA Once one has achieved a state where the desired products are single stranded and the undesired products are double stranded, one can lock the double stranded nucleic acids by permanent or semipermanent (i.e., stable) cross-linking (FIG. 2). Cross-linked double stranded DNA will subsequently be an inert player in most reactions that require a single stranded form, such as nucleic acid hybridization, interaction with certain fluorescent dyes specific to single stranded nucleic acids, PCR and PCR's various modified forms.

Essentially what has been achieved through the cross-linking, therefore, is the inhibition of further activity by the now unnecessary complements and the isolation of the desired product for further testing or other uses.

Using PCR Misbalancing and Cross-Linking to Detect Small Differences in Nucleic Acid Content Detecting small differences in nucleic acid content or providing accurate quantification of low concentration nucleic acids is an important goal for a wide range of diagnostic and research approaches. The method described below compares the relative concentration of two nucleic acids by eliminating the common background through stoichiometric pairing (which need not be one to one). The description that follows discusses the one to one pairing of nucleic acids and refers for illustration purposes to FIG. 3 and the notation used in FIG. 3.

For this approach, assume that the two nucleic acids, a target (ABC) and a reference (DEF) to be compared to each other are at low concentrations. By performing PCR, the quantity of the desired sequences can be increased. Now assume that this PCR step is performed such that the reverse primer (F') for the reference has been modified to include a partial sequence (pB) that is approximately equivalent to a region on the target template (B). By approximately equivalent, is meant that a complement of the approximately equivalent partial sequence (pB') would bind a desired region of the original sequence on the target to template (B). This reverse primer for the reference template is referred to as pBF'.

After several PCR steps e.g., 2, 3, 4, 5, 10, 15, etc., the products shown in Step 2 of FIG. 3 will be found in the mixture. The difficulty lies in that many future analyses are prohibited by the presence of numerous fragments that can bind to our desired product, inhibiting many methodologies later on. This is where misbalancing the PCR reaction becomes important.

By adding excess complements (C, F) to both the reverse primer of the target (C') and the reverse primer of the reference (F') and establishing hybridization conditions, the double stranding of these primers is favored. If the conditions are right, a subsequent extension on the reverse primer will double strand the pB region with a pB' complement. C and F are referred to as disruption sequences. The disruption sequences will not stop with double stranding both reverse primers under hybridizing/extending conditions. They will also bind to the complement templates (C'B'A' and pBF'E'D'), and on the reference template there will be a short extension to double strand the pB sequence. The forward primers will not remain inactive either. They will eventually (although statistically later due to relative concentrations) find the complement templates as well and by hybridization and extension, they will double strand the rest of the complement template with a small discontinuation in the new double strand where the extension of the forward primers meets the disruption sequences.

Now that the higher concentration disruption primers and forward primers did their work, the original templates find time and space to bind to each other and extend in a predefined 1 to 1 ratio. What remains are shown in Step 3 of FIG. 3. Due to the 1 to 1 pairing of the original templates, if there is an excess of the target, there will be single stranded ABCs left over. If there is an excess of the reference, there will be single stranded DEFpB' left over. Even if the template pairing reaction is not perfect, the relative difference between the target and reference template will be increased by maintaining the absolute difference and reducing the common background by equal absolute amounts.

A next step is to "hide" the double stranded nucleic acids from further reactions. This can be accomplished, for example, by selectively, physically removing them, enzymatically degrading them, or cross-linking them. In Step 4 of FIG. 3 the "hiding" of the double stranded nucleic acids by permanently or semi-permanently cross-linking them to each other is shown. If the detection method that follows is specific for single stranded DNA or DNA that is capable of becoming single stranded, one has successfully removed interactions from all double stranded entities.

One detection tool that works well after permanent or semi-permanent cross-linking is PCR. Large relative differences of even small quantities of nucleic acids can be easily detected by PCR, although it is necessary to prevent further cross-linking of double stranded molecules for PCR. In the preceding description, the forward primers for both the target and the reference templates (A and D, respectively) are already present. One need only add new reverse primers (FIG. 4).

The above methodology could be simply modified such that the target and reference are reversed, or to focus on recovering the complements, rather than the original template sequences.

In another embodiment, one can create systems where the reference nucleic acid that the target is being compared to is part of a standard dilution with known concentration. This would allow for accurate bounding of nucleic acid concentrations by determining which two standard concentrations the target nucleic acid falls between and potentially by looking at the final relative amounts of target and reference, and estimating, for example, the distance from either or both standards.

Nucleic Acid Sample:

The nucleic acid sample to which the methods described herein are applied can be from any source. Frequently, the sample can be a biological material which is isolated from its natural environment and contains a polynucleotide. A sample can consist of purified or isolated polynucleotide, or it can comprise a biological sample such as a tissue sample, a biological fluid sample, or a cell sample comprising a polynucleotide. A biological fluid includes, as non-limiting examples, blood, plasma, sputum, urine, cerebrospinal fluid, lavages, and leukophoresis samples. A nucleic acid sample can be derived from a plant, animal, bacterial or viral source. Samples can be obtained from differing sources, including, but not limited to, samples from different individuals, different developmental stages of the same or different individuals, different diseased individuals (e.g., individuals with cancer or suspected of having a genetic disorder), normal individuals, different disease stages of the same or different individuals, individuals subjected to different disease treatment, individuals subjected to different environmental factors, or individuals with predisposition to a pathology, or individuals with exposure to an infectious disease agent (e.g., HIV).

Samples can also be obtained from in vitro cultured tissues, cells, or other polynucleotide-containing sources. The cultured samples can be taken from sources including, but not limited to, cultures (e.g., tissue or cells) maintained in different media and conditions (e.g., pH, pressure, or temperature), cultures (e.g., tissue or cells) maintained for different periods of length, cultures (e.g., tissue or cells) treated with different factors or reagents (e.g., a drug candidate, or a modulator), or cultures of different types of tissue or cells.

Furthermore, samples can be obtained as a product of polynucleotide synthesis.

The sample preferably comprises isolated nucleic acid from a source as described above. Methods of isolating nucleic acids from biological sources are well known and will differ depending upon the nature of the source. One of skill in the art can readily isolate nucleic acid from a source as needed for the methods described herein. In some instances, it can be advantageous to fragment the nucleic acid molecules in the nucleic acid sample. Fragmentation can be random, or it can be specific, as achieved, for example, using restriction endonuclease digestion. Methods for random fragmentation are well known in the art, and include, for example, limited DNAse digestion, alkali treatment and physical shearing.

In one embodiment, the sample is collected from a pregnant female, for example a pregnant woman. In this instance, the sample can be analyzed using the methods described herein to prenatally diagnose chromosomal abnormalities in the fetus. The sample can be collected from biological fluids, for example the blood, serum, plasma, or some fraction thereof. In a preferred embodiment, the sample consists of purified nucleic acid isolated from the blood of a pregnant woman.

Analysis of blood plasma DNA has revealed that it is composed mainly of short DNA fragments, and interestingly, the average fragment size was greater in pregnant women than in nonpregnant women. Furthermore, it seems that fetal fragments in pregnant women's plasma DNA were shorter on average than maternal fragments (Chan et al., 2004, Clin. Chem. 50: 88-92). Methods for the isolation of nucleic acid from blood, serum or processed fractions thereof are well known in the art. Methods of isolation of nucleic acids from blood or serum are described in, for example Chen et al., 1996, Nature Med. 2: 1033-1035 and Lo et al., 1997, Lancet 350: 485-487. The Lo et al. reference specifically recognized the presence of fetal DNA in maternal plasma and serum. Further, Dhallan et al. (2004, J.A.M.A. 291: 1114-1119) and WO 95/08646 describe methods to enrich for fetal DNA from maternal serum. While such enrichment is not necessary for the prenatal diagnostic embodiments described herein, the potential for such enrichment could be advantageous in some aspects of the methods described herein. Fetal cells can also be selected and obtained from the maternal circulation (see e.g., Bischoff et al., Hum. Reprod. Update 8, 493-500 (2002) and Merchant et al., Hum. Reprod. Update 8, 509-521 (2002), and can serve as a source for target and reference nucleic acid sequences. For example, sorted fetal cells can serve as the source for target and reference sequences obtained by PCR (see e.g., Geifman-Holtzman et al., Am. J. Obstet. Gynecol. 174:818-22 (1996)). If the fetus is male, then another approach is to use a reference sequence from the Y chromosome; such sequences can be obtained from cell-free fetal DNA in the maternal circulation (see e.g., Sekizawa et al., Am. J. Pharmacogenomics 1:111-7 (2001).

In addition to the early detection of birth defects, the methods described herein can be applied to the detection of any abnormality in the representation of genetic sequences within the genome. It has been shown that blood plasma and serum DNA from cancer patients contains detectable quantities of tumor DNA (Chen et al., 1996, Nature Med. 2: 1035; Nawroz et al., 1996, Nature Med. 2: 1035-1037). Tumors are characterized by aneuploidy, or inappropriate numbers of gene sequences or even entire chromosomes. The detection of a difference in the amount of a given sequence in a sample from an individual can thus be used in the diagnosis of cancer.

Target Nucleic Acid:

The methods described herein facilitate the detection of differences in the amount of a target nucleic acid versus a reference nucleic acid sequence. Target nucleic acids include any nucleic sequence that is associated with a difference in sequence representation in healthy versus diseased individuals. Genomic DNA is especially useful as a source of target and reference nucleic acids. Thus, a target nucleic acid sequence can be a sequence on a chromosome that is misrepresented in a disease, e.g., a sequence on a chromosome noted in Table 1.

Target sequences also include, for example, sequences known to exist in a polymorphic state. Target sequences can also include, for example, sequences known to be amplified or over-represented not in the whole individual, but in certain cells of the individual, as is seen for example, in cells of some cancers.

Finally, target sequences also include sequences under investigation, for example, for differential gene expression. The amount of an RNA transcript can be measured relative to a reference sequence by applying the methods described herein to a sample containing reverse-transcription reaction products of the RNA source of interest.

Reference Nucleic Acid:

The reference nucleic acid called for in the methods described herein is a sequence against which the amount of a target sequence is compared. Most often, a reference sequence will be one having a known or expected representation in the nucleic acid sample. For genomic DNA, for example, a reference sequence can be a sequence that is present in a single copy per genome, e.g., in heterozygous individuals, or in two copies, e.g., in homozygous individuals. Where the target sequence is to be measured in RNA, for example to determine the level of expression of a given message, the reference can be, for example, a housekeeping gene sequence, e.g., GAPDH, actin or a histone sequence, or another sequence for which the level is known, or at least which is known to be relatively invariant.

Most often, a reference sequence will be one that is already present in a biological sample, preferably at a known representation. For example, where one wishes to investigate the amount of a sequence associated with a genetic disorder, such as chromosome 21 trisomy indicative of Down syndrome, the reference sequence would be a sequence not present on chromosome 21, while the target sequence would be a sequence present on chromosome 21. In this example, where the reference sequence is present in two copies (a homozygous sequence), if the target sequence is found to be more abundant in maternal serum than the reference sequence using the methods described herein, the data would be indicative of Down syndrome in the fetus.

Alternatively, the reference sequence can be one that is spiked into the sample at a known or constant amount and which differs from the target sequence. This approach will give results that indicate the amount of target sequence relative only to the amount of external spiked reference sequence, but can be used to normalize between samples the levels of another reference sequence that is internal to the sample. The use of internal standard sequences is especially useful for determining and correcting for differences in amplification efficiency, as is generally known in the art.

Probes:

Probes for use in the methods described herein will refer to the single stranded amplified target and reference template or complement, depending on which set is under further investigated. These probes could be exact PCR amplified copies or complements of the original sequences, or they could exhibit modifications introduced during the initial PCR steps. Target probe will correspond to the sequence under investigation that was derived from the target sequence. Reference probe will correspond to the sequence under investigation that was derived from the reference sequence.

Binding Partners:

In each instance, a probe will also comprise a region or moiety that permits the physical pairing of target and reference probes under certain conditions.

The region or moiety (referred to as a "binding partner moiety") that permits physical pairing will comprise a means of specifically binding one probe (under certain conditions) to a probe that binds another nucleic acid sequence. This ability of the target probe to bind the reference probe permits the "removal" or sequestration of a proportional number of target and reference probes. This "removal" permits the detection of non-paired target or reference sequence that is indicative of a difference in the amount of one sequence versus the other in the nucleic acid sample.

In a preferred aspect, a region or moiety for binding a reference probe to a target probe is made by incorporating a corresponding member of a specific binding partner pair into each of a target and a reference probe. Binding partners can interact by, for example, hybridization (involving hydrogen bonding), protein interactions, covalent bonding, ionic bonding, van der Waals interactions and hydrophobic interactions. The binding partners will necessarily bind to each other with a well-defined stoichiometry. This is not to say that the binding partners bind with 1:1 stoichiometry. Rather, what is important is that the stoichiometry be known. For example, avidin binds biotin with up to 8:1 stoichiometry. However, the biotin:avidin stoichiometry actually observed can vary depending upon the influences of steric hindrances caused by the appended nucleic acid sequence(s). For a given biotinylated probe, however, the stoichiometry of avidin or streptavidin binding is expected to remain constant.

Binding partners useful in the methods described herein are preferably conditionally able to bind to each other. By "conditionally able to bind to each other" is meant that the binding of one partner to the other can be manipulated such that detectable binding only occurs when one wishes for it to occur. The conditional aspect can be manipulated by, for example, changing temperature, salt or some other physical or chemical parameter of the environment. For example, lowering the temperature of a solution below the $T_m$ for a nucleic acid binding pair renders the pair able to bind each other. Conditional binding can also be achieved by competition for the binding sites by easily "removable" competitors. By "removable" competitors is meant molecules that compete for the binding of the probes to each other, but that can be either physically removed or made inert when it is desired to permit the probes to bind to each other.

Conditional binding can also be achieved through the addition of a catalyst that causes binding. For example, the exposure of complementary sequences comprising halogenated nucleosides to UV can result in the covalent cross-linking of the sequences. Chemical cross-linking agents are also known to those of skill in the art.

In one embodiment, the binding partners are substantially complementary nucleic acid sequences comprises by the respective probes. In this aspect, the binding partner nucleic acid sequence on one probe is able to hybridize to the binding partner nucleic acid sequence on the other probe under a given set of conditions.

Similar parameters to those considered in designing PCR primer sequences are considered in designing the sequences of binding partner nucleic acid sequences to include on probes as described herein. For example, one of skill in the art will consider the impact of length and G+C content on the hybridization behavior of the binding partner sequences. Often, although not necessarily, the binding partner sequence of a probe that uses a nucleic acid as a binding partner will be of equal or shorter (e.g., at least one nucleotide or more shorter) length than that portion of a probe that binds the reference or target sequence.

Binding partners can alternatively be respective members of any specific binding pair that is compatible with the environment required for nucleic acid hybridization. That is, the binding partner moieties can also interact through means other than hybridization. For example, the binding partner moieties can be a pair of moieties that bind to each other through covalent or non-covalent interactions. Examples of such binding partner moieties include but are not limited to: biotin-streptavidin, biotin-avidin, receptor-ligand pairs, heterodimerization motif pairs (e.g., complementary leucine zipper motifs, complementary helix-loop-helix motifs, etc.), antigen-antibody interactions, aptamer-ligand interactions, or multi-component chemical reactions. Methods for the linkage of non-nucleic acid binding partners to probes are well known in the art. Further, one skilled in the art can readily determine whether the environment required for nucleic acid hybridization has an adverse effect on the binding partner moieties or their abilities to bind each other.

The binding partner moieties can also interact indirectly through an "adapter molecule." As used herein, an adapter molecule is any molecule which is capable of binding specifically to the binding partner moieties, thereby bridging the reference and target probe sequences. In one embodiment, the adapter molecule comprises nucleic acid sequences that can hybridize to nucleic acid binding partner moieties of the first and second probe. The adapter molecule can be single-stranded, double-stranded or double-stranded with one or more overhangs. As one non-limiting example of an adapter, a double stranded nucleic acid with two different single-stranded overhangs could be used—one overhang would be substantially complementary to a binding partner sequence on the target probe, and the other would be substantially complementary to a binding partner sequence on the reference probe. The adapter molecule can also comprise multiple nucleic acids.

When using an adapter molecule, it is preferable that the sites which interact with the binding partner moieties are able to distinguish between the binding partner moieties of the first and second probe. It is also preferable that the ratio of first and second probes with which each adapter molecule can interact be a defined number. In one embodiment, the adapter molecule is able to bind the first and second probe at a ratio of 1:1.

It is not necessary that an adapter molecule interact with the first and second probes at a 1:1 ratio. In alternative embodiments, a single adapter molecule can bind to multiple copies (e.g., 2, 3, 4, 5, 6, 7, 8, etc.) of the first and second probes. For example, the adapter molecule can comprise a solid support containing a plurality of sites with which the first and second probes can specifically interact. As a non-limiting example, the binding partner moiety of the first probe may consist of a poly-A tail, and the binding partner moiety of the second probe may consist of a poly-C tail. The adapter molecule can comprise a solid support, for example a bead, comprising a plurality of poly-T and poly-G oligonucleotides, to which the first and second probe can specifically interact through their binding partner moieties, respectively. In another alternative embodiment, more than one (e.g., 2, 3, 4, 5, 6, 7, 8, etc.) adapter molecule can be employed.

Sequestration or Removal of Target:Reference Probe complexes:

The methods described herein exploit the formation of complexes between a reference probe and a target probe. In order to detect non-complexed or "left over" probe molecules after the probes are bound to each other, it can be advantageous to remove, "hide" or sequester the target:reference probe complexes. There are several ways to accomplish this removal, "hiding" or sequestration.

One approach is to "hide" the target:reference probe complexes from detection. This can be achieved by permanent cross-linking of the target:reference probes in such a way that it interferes with the detection method. For example, if PCR is used for the detection of impaired probes, complementary sequences on the target and reference probe can be used to bind them and this duplex can be cross-linked by chemical or physical means, such as UV, mitomycin C, or others described previously. If the primers for the detection are designed to overlap the permanent crosslink site or can be found on opposite sides of the crosslink sites, PCR amplification of paired probes will be inhibited, thus only unpaired probes will be amplified, and thus detected.

Introducing halogenated nucleosides (e.g., to the PCR primers or disruption sequences) can improve U.V. crosslinking efficiencies (see Qiagen website). Other useful chemical modifications to nucleosides or nucleotides include, as non-limiting examples, thiolation, amidation and biotinylation. More than one (e.g., 2, 3, 4 or more) primer in the reaction can be modified if desired, including different modifications to different primers. Chemical crosslinkers can also be used, such as mitomycin C (Bizanek et al. Biochemistry 1992, 31, 3084-3091) or derivatives of it, nitric oxide (Caulfield et al. Chem Res Toxicology, 16(5):571-574, 2003), pyrrole/imidazole CPI conjugates (Bando et al., J. Am. Chem. Soc., 2003, 125, 3471-3485), carzinophilin, bizelesin, nitrogen mustard, netropsin or derivatives of these. As noted above, the cross-linked hybrids are not effective templates for detection by, for example, PCR. Therefore, PCR using primers that amplify target and/or reference probes or sequences will yield amplification products only where there is non-cross-linked template sequence. As discussed herein with regard to final detection methods, amplification primers should be designed so they will either hybridize to the to region at which probes become cross-linked or so that the amplification sequence would contain the cross-linked region, thus inhibiting PCR strand extension. In either instance the presence of cross-linked probe will interfere with PCR amplification, and therefore the readout of the PCR will correspond to the sequences not crosslinked through these methods.

Detection of Unpaired Probes:

Following the physical pairing of target and reference probes in proportion to the amount of target sequence present, the methods described herein require the detection of unpaired probes. This detection can be performed by one of several different approaches.

One method of detecting unpaired probe uses polymerase chain reaction (PCR) amplification of probe molecules that are available to serve as amplification templates. PCR is well known in the art, and uses a thermostable template dependent polymerase and oligonucleotide primers that anneal to template nucleic acid on opposite strands in cycles of primer annealing, primer extension and strand separation to generate exponentially increasing numbers of duplicate copies of a template sequence. See, for example, Mullis et al., U.S. Pat. No. 4,683,202.

PCR detection of unpaired probes can be performed through use of PCR primers that amplify the unpaired probe sequences. PCR primers can be designed so as to exploit the nature of the unpaired probes. For example, where the target and reference probes bind to each other through hybridization of complementary sequence tags, one of the primers used for unpaired probe amplification can be designed to be complementary to the sequence tag. If, for example, the target and reference probes are cross-linked to each other after hybridization of the complementary sequence tags, the tags of the cross-linked molecules will not be available for amplification primer binding, which will exclude the cross-linked probes from amplification using a primer that hybridizes to the tag. Such an approach would leave only the unpaired probes available for amplification and subsequent detection.

The detection of PCR product indicative of unpaired probe and a difference in the amount of target nucleic acid can be by any means commonly used to detect PCR products. For example, PCR can incorporate a fluorescent or radiolabeled nucleotide or primer, and fluorescence or isotope detection can be used to obtain a read out. Alternatively, a real time method such as the TaqMan™ and Molecular Beacon methods, or related methods, can be used.

In the TaqMan assay (see e.g., U.S. Pat. No. 5,723,591), two PCR primers flank a central probe oligonucleotide. The probe oligonucleotide comprises two fluorescent moieties. During the polymerization step of the PCR process, the polymerase cleaves the is probe oligonucleotide. The cleavage causes the two fluorescent moieties to become physically separated, which causes a change in the wavelength of the fluorescent emission. As more PCR product is created, the intensity of the novel wavelength increases.

Molecular Beacons (see U.S. Pat. Nos. 6,277,607; 6,150,097; 6,037,130) are an alternative to TaqMan. Molecular Beacons undergo a conformational change upon binding to a complementary template. The conformational change of the Beacon increases the physical distance between a fluorophore moiety and a quencher moiety on the Beacon. This increase in physical distance causes the effect of the quencher to be diminished, thus increasing the signal derived from the fluorophore.

Other applicable fluorescent and enzymatic PCR technologies, such as Scorpions™ (Solinas et al., 2001, Nucleic Acids Res. 29: e96), Sunrise™ primers (Nazarenko et al., 1997, Nucleic Acids Res., 25, 2516-2521), and DNAzymes can also be used.

PCR-based detection of unpaired probes can also use capillary electrophoresis for rapid detection. Generally, where capillary electrophoresis is used, amplification of a sequence incorporates a fluorescent nucleotide or primer that is then detected as sample passes through the capillary.

Capillary electrophoresis can also be used without the need for PCR amplification if the signal from the unpaired probes is sufficient for a reliable signal. Alternatively, fluorescence tags or fluorescence tag "dockers" could be used that selectively bind unpaired probes. By fluorescence tag "dockers" are meant entities that can bind a predetermined number of fluorescent tags either directly or through adapter molecules to aid in detection. Yet another method is to add inactive enzymes that can be activated either directly, or through adapter molecules by the unpaired probes selectively. Enzyme activity can then be detected by a change in color, fluorescence or similar readout. Other detection methods could include radioactive tagging and other methods.

Chromosome Abnormalities and Disease:

In the methods described herein, deviations from a 1:1 ratio of target to reference gene indicates a likely chromosomal abnormality. Non-limiting examples of chromosome abnormalities that are associated with disease and which can be evaluated using the method according to the methods described herein are provided in Table 1 below.

TABLE 1

Chromosome Abnormalities and Disease

| | Chromosome Abnormality | Disease Association |
|---|---|---|
| X, Y | XO | Turner's Syndrome |
| | XXY | Klinefelter syndrome |
| | XYY | Double Y syndrome |
| | XXX | Trisomy X syndrome |
| | XXXX | Four X syndrome |
| | Xp21 deletion | Duchenne's/Becker syndrome, congenital adrenal hypoplasia, chronic granulomatus disease |
| | Xp22 deletion | steroid sulfatase deficiency |
| | Xq26 deletion | X-linked lymphproliferative disease |
| 1 | 1p-(somatic) | neuroblastoma |
| | monosomy | |
| | trisomy | |
| 2 | monosomy | |
| | trisomy 2q | growth retardation, developmental and mental delay, and minor physical abnormalities |
| 3 | monosomy | |
| | trisomy (somatic) | non-Hodgkin's lymphoma |
| 4 | monosomy | |
| | trsiomy (somatic) | Acute non lymphocytic leukaemia (ANLL) |
| 5 | 5p- | Cri du chat; Lejeune syndrome |
| | 5q-(somatic) | myelodysplastic syndrome |
| | monosomy | |
| | trisomy | |
| 6 | monosomy | |
| | trisomy (somatic) | clear-cell sarcoma |
| | 7q11.23 deletion | William's syndrome |
| | monosomy | monosomy 7 syndrome of childhood; somatic: renal cortical adenomas; myelodysplastic syndrome |
| | trisomy | |
| 8 | 8q24.1 deletion | Langer-Giedon syndrome |
| 8 | monosomy | |
| | trisomy | myelodysplastic syndrome; Warkany syndrome; somatic: chronic myelogenous leukemia |

TABLE 1-continued

Chromosome Abnormalities and Disease

| | Chromosome Abnormality | Disease Association |
|---|---|---|
| 9 | monosomy 9p | Alfi's syndrome |
| | monosomy | |
| | 9p partial trisomy | Rethore syndrome |
| | trisomy | complete trisomy 9 syndrome; mosaic trisomy 9 syndrome |
| 10 | monosomy | |
| | trisomy (somatic) | ALL or ANLL |
| 11 | 11p- | Aniridia; Wilms tumor |
| | 11q- | Jacobson Syndrome |
| | monosomy (somatic) | myeloid lineages affected (ANLL, MDS) |
| | trisomy | |
| 12 | monosomy | |
| | trisomy (somatic) | CLL, Juvenile granulosa cell tumor (JGCT) |
| 13 | 13q- | 13q-syndrome; Orbeli syndrome |
| | 13q14 deletion | retinoblastoma |
| | monosomy | |
| | trisomy | Patau's syndrome |
| 14 | monsomy | |
| | trisomy (somatic) | myeloid disorders (MDS, ANLL, atypical CML) |
| 15 | 15q11-q13 deletion | Prader-Willi, Angelman's syndrome |
| | monosomy | |
| | trisomy (somatic) | myeloid and lymphoid lineages affected, e.g., MDS, ANLL, ALL, CLL) |
| 16 | 16q13.3 deletion | Rubenstein-Taybi |
| | monosomy | |
| | trisomy (somatic) | papillary renal cell carcinomas (malignant) |
| 17 | 17p-(somatic) | 17p syndrome in myeloid malignancies |
| | 17q11.2 deletion | Smith-Magenis |
| | 17q13.3 | Miller-Dieker |
| | monosomy | |
| | trisomy (somatic) | renal cortical adenomas |
| | 17p11.2-12 trisomy | Charcot-Marie Tooth Syndrome type 1; HNPP |
| 18 | 18p- | 18p partial monosomy syndrome or Grouchy Lamy Thieffry syndrome |
| | 18q- | Grouchy Lamy Salmon Landry Syndrome |
| | monosomy | |
| | trisomy | Edwards Syndrome |
| 19 | monosomy | |
| | trisomy | |
| 20 | 20p- | trisomy 20p syndrome |
| | 20p11.2-12 deletion | Alagille |
| | 20q- | somatic: MDS, ANLL, polycythemia vera, chronic neutrophilic leukemia |
| | monosomy | |
| | trisomy (somatic) | papillary renal cell carcinomas (malignant) |
| 21 | monosomy | |
| | trisomy | Down's syndrome |
| 22 | 22q11.2 deletion | DiGeorge's syndrome, velocardiofacial syndrome, conotruncal anomaly face syndrome, autosomal dominant Opitz G/BBB syndrome, Caylor cardiofacial syndrome |
| | monosomy | |
| | trisomy | complete trisomy 22 syndrome |

Generally, evaluation of chromosome or gene sequence dosage is performed in conjunction with other assessments, such as clinical evaluations of patient symptoms. For example, prenatal evaluation may be particularly appropriate where parents have a history of spontaneous abortions, still births and neonatal death, or where advanced maternal age, abnormal maternal serum marker results, or a family history of chromosomal abnormalities is present. Postnatal testing may be appropriate where there are multiple congenital abnormalities, clinical manifestations consistent with known chromosomal syndromes, unexplained mental retardation, primary and secondary amenorrhea, infertility, and the like.

Detecting Diseases and Disorders

As described above, the methods described herein can detect differences between nucleic acid concentrations. As such, the methods can be used to detect diseases and disorders that are linked to a genetic imbalance in DNA or RNA concentrations. To do so, one need only define what the deviation from normal is that describes the disease. Given the following possible scenarios, examples of potential solutions using the above methods follow:

The Target Concentration is Normally Equal to an Internal Reference, but in Case of Disease, the Concentration of the Target Relative to the Reference Decreases or Increases:

The target and the reference in this case, once extracted from a biological sample, is equivalent to the target and reference, respectively, in the above analysis. The starting samples are prepared in such a manner that the relative amounts of target and reference is maintained, therefore allowing one to perform the steps described in the previous section. The final PCR detection step detects whether the target and the internal reference are equal or, alternatively, whether there is a deviation in the concentration of the target as compared to the reference. This knowledge is indicative of the underlying presence or absence of a disease or disorder.

The Target Concentration is Normally Less (More) than an Internal Reference, but in Case Of the Disease, the Concentration of the Target Becomes Relative More (Less) than the Internal Reference:

The target and the reference in this case, once extracted from a biological sample, is equivalent to the target and reference, respectively, in the above analysis. The starting samples are prepared in such a manner that the relative amounts of target and reference are maintained, therefore allowing one to perform the steps described in the previous section. The final PCR detection step detects whether the target concentration is greater than or less than that of the internal reference. This knowledge is indicative of the underlying presence or absence of a disease or disorder.

The Target Concentration is Normally Less (More) than a Threshold Concentration X, but In Case of the Disease, the Concentration of the Target Becomes More (Less) than the Threshold Concentration X:

The target in this case, once extracted from a biological sample, is equivalent to the target in the above analysis. The reference is an external standard added at the threshold concentration X. The starting samples are prepared in such a manner that the relative amounts of target and reference is maintained, therefore allowing one to perform the steps described in the previous section. The final PCR detection step detects whether the target concentration is greater than or less than that of the reference, which is at the threshold concentration X. This knowledge is indicative of the underlying presence or absence of a disease or disorder.

Detecting Down Syndrome or Other Genetic Disorders from Free Fetal DNA Found in Maternal Serum or Plasma 1 in 20 babies are born with a genetic disorder. Down syndrome is the most common chromosomal disorder affecting about 1 in 750 births (Table 2). The incidence of Down syndrome is increasing with the increasing average age at which women are bearing children.

TABLE 2

Incidence and inheritance of fetal aneuploidy.

| Disorder | Incidence | Inheritance |
| --- | --- | --- |
| Down syndrome | 1 in 750 births | Trisomy 21 |
| Edward syndrome | 1 in 3,000 births | Trisomy 18 |
| Patau syndrome | 1 in 5,000 births | Trisomy 13 |
| Klinefelter syndrome | 1 in 1,000 births | 47, XXY |
| Turner syndrome | 1 in 3,000 births | 45, XO |
| XYY syndrome | 1 in 1,000 births | 47, XYY |
| Triple-X syndrome | 1 in 1,000 births | 47, XXX |

Down syndrome is caused by trisomy 21—an occurrence of three instead of the normal two copies of chromosome 21. Down patients suffer from mental retardation, heart defects, premature death, and anatomical deformities; most require a lifetime of care. They pose an immense emotional, physical and financial strain on the families and society. Many women therefore want a choice about bringing a child with Down's syndrome into the world or to prepare emotionally for the birth.

Down syndrome is an example of a disease in which early detection is desirable. The tests used today are amniocentesis, chronic villus sampling (CVS), umbilical cord sampling, fetal biopsy, and maternal serum, urine, and ultrasound screens.

Amniocentesis is an invasive test requiring an ultrasound-guided needle biopsy of the amniotic fluid surrounding the fetus, through the mother's abdomen. Fetal cells from the amniotic fluid are cultured, and the chromosomes are visualized by fluorescent in-situ hybridization (FISH). Results take 2-4 weeks. Amniocentesis is only recommended between 15 and 18 weeks of pregnancy. It carries a 1% chance of miscarriage and a slight increase in risk of limb disorders. Amniocentesis is estimated to have a sensitivity of 99.3% and a specificity of 99.9%.

Serum screens for Down syndrome are non-invasive tests that measure the level of particular serum markers. Markers include alpha-fetoprotein (AFP), human chronic gonadotropin (hCG), unconjugated estriol, inhibin A, and PAPP-A. Most markers are tested between the 16th and 18th week of pregnancy, and their combinations have less than 75% sensitivity at a 95% specificity.

In 1979 it was found that maternal blood contains fetal red blood cells (fRBC), but no commercial diagnostics to date have utilized this knowledge. In 1997, free fetal DNA was also found in maternal blood serum and plasma (U.S. Pat. No. 5,641,268). These fetal cell and DNA, however, are diluted by significant amounts of maternal cells and DNA (Lo et al., J. Hum Genet. 1998 62, 768-75), complicating the detection of fetal genetic abnormalities.

Nevertheless, free fetal DNA found in maternal blood serum and plasma has been hypothesized to be present in average relative concentrations (as compared to maternal DNA) of up to 20-25% on average (Dhallan et al, JAMA 291:1114-1119, 2004. Benachi, Clin Chem 51:1-3, 2004. Lo et al, Am J Hum Genet. 64:218-224, 1999.). A 20% fetal, 80% maternal DNA mixture of a healthy mother and a fetus with Down syndrome will result in a 10% greater chromosome 21 DNA content than a reference chromosome content, for example, chromosome 10 DNA content. This 10% difference can be detected by the above methods.

Once the free DNA has been isolated from maternal blood serum or plasma, one can perform a method as described herein upon it to determine the relative amounts of target and reference sequence. For detection of Down syndrome, for example, one would choose a target sequence on chromosome 21 and a reference sequence on any other chromosome, e.g., chromosome 10. The operative question is whether the concentration of the target sequence is equal to the reference sequence concentration, indicative of a healthy fetus, or whether the target sequence can be found in excess as compared to the reference sequence, which is indicative of Down Syndrome. The results of the above methodology provide a measurement of this relative concentration, providing a method to detect fetal Down syndrome from a maternal blood sample. This approach is applicable to a wide range of such genetic disorders.

Description of additional methods and materials that further support the new methods described herein is provided in U.S. patent application Ser. No. 11/036,833, filed Jan. 14, 2005, and in U.S. patent application No. 60/622,522, filed Oct. 27, 2004, the entirety of both of which is incorporated herein by reference.

EXAMPLES

Example 1

Detection of the amount of a Chromosome 18 sequence relative to a Chromosome 10 sequence using biotin immobilization of the reference The methods described herein are applied to the detection of trisomy 21 in maternal serum as follows. The target and reference probes used are as follows (nomenclature is as in FIG. 3):
Target sequence from 18q:

```
                                              (SEQ ID NO: 2)
5'-GAGGAGACCAGGGGCTCAAGTGAGCCCCTCCGAGGGGATGGCTGTGC

TGCAGCAGAGATATGACTAGAGACAACCCTCCTGGGCCGACTGCTAGAGA

ACAGCAGCGCCACTGTTGCGTCT-3'
``` where the first line will be equivalent to sequence A, second and third line are equivalent to sequence B, the third line is also equivalent to pB, and the fourth line is equivalent to C as shown in FIG. 3.

Reference Sequence from 10p:

```
                                              (SEQ ID NO: 3)
5'-ACAAGCTGCAAGCTCACGACTTACCATTCCGTAACGCTTTTATGGGC

TCTGATGACCGAGGTCTCAATGTCGATTGGGTGGT-3'
``` where the first line is equivalent to sequence D, the second line is equivalent to sequence E, and the third line is equivalent to sequence F as shown in FIG. 3.

The above sequences are first amplified by PCR. The primers used are:

```
Target forward primer (A):
                                              (SEQ ID NO: 4)
5' - GAGGAGACCAGGGGCTCAAG - 3'

Target reverse primer (C'):
                                              (SEQ ID NO: 5)
5' - AGACGCAACAGTGGCGCTGC - 3'

Reference forward primer (D):
                                              (SEQ ID NO: 6)
5' - ACAAGCTGCAAGCTCACGAC - 3'

Reference reverse primer (pBF'):
                                              (SEQ ID NO: 7)
5' - GGGCCGACTGCTAGAGAACAACCACCCAATCGACATTGAG - 3'
```

The reference reverse primer's first half is a 20 bp sequence that is equivalent to the third line sequence of the target sequence as shown above. Note that this is sequence pB according to FIG. 3.

For this PCR amplification step, one starts with 5 µl of target and reference sequences serving as templates, then add 10 µl of primer solution with 450 nM of each primer, and a 15 µl of 2×PCR mix (e.g. Advanced Biotechnologies buffer IV). Exemplary PCR cycling conditions are as follows:
  a. 95° C. for 15 minutes (activate enzyme if necessary)
  b. cycle 10-20 times the following:
    i) 94° C. for 20 seconds
    ii) 55° C. for 30 seconds
    iii) 72° C. for 40 seconds
  c. Hold at 4° C.

After retrieving the above post-PCR mixture, one adds the disrupt sequences at 10 µM final concentration as described above:

```
Target disrupt sequence (C):
                                              (SEQ ID NO: 8)
5' - GCAGCGCCACTGTTGCGTCT - 3'

Reference disrupt sequence (F):
                                              (SEQ ID NO: 9)
5' - CTCAATGTCGATTGGGTGGT - 3'
```

This is followed by another heat cycle:
  d. 95° C. for 15 minutes (activate enzyme if necessary)
  e. only once perform the following:
    i) 94° C. for 20 seconds
    ii) 55° C. for 30 seconds
    iii) 72° C. for 40 seconds
    iv) 55° C. for 1 hour
    v) 72° C. for 40 seconds
  f. Hold at 4° C.

To the misbalanced PCR mixture, one can then add a mitomycin dimer as shown below (picture of dimer taken from Paz et al., J Med Chem, 47:3308-3319, 2004) at a final concentration of 100 µM:

The mitomycin dimer is activated using acidic pH (pH 4.0) and the samples are incubated for 3 hours to achieve maximum efficiency cross-linking. After the cross-linking step, neutral pH is reestablished to enable another PCR reaction.

Aliquots of the cross-linked samples from above are then used in another round of PCR. Since the previous PCR and hence the solution already contain the necessary forward primers, one need only to add two new reverse primers (FIG. 4). These are, e.g.:

```
R1 primer:
                                              (SEQ ID NO: 10)
5' - AGGAGGGTTGTCTCTAGTCA - 3'

R2 primer:
                                              (SEQ ID NO: 11)
5' - GGGCCGACTGCTAGAGAACA - 3'
```

Using the new reverse primers, the old forward primers and the sample aliquot from the cross-linked mixture, one then adds 2×PCR mix in equal volumes to perform a round of real-time PCR using multiplexed Taqman probes to detect the relative concentration of the target and the sequence probes. Again, a sample PCR heat cycle is:
  a. 95° C. for 15 minutes (activate enzyme if necessary)
  b. Cycle 50 times the following:
    i) 94° C. for 20 seconds
    ii) 55° C. for 30 seconds
    iii) 72° C. for 40 seconds
  c. Hold at 72° C. for 15 seconds
  d. Hold at 4° C.

Other Embodiments

Other embodiments will be evident to those of skill in the art. It should be understood that the foregoing detailed description is provided for clarity only and is merely exemplary. The spirit and scope of the present invention are not limited to the above examples, but are encompassed by the following claims.

The invention claimed is:

1. A method of determining which of a target nucleic acid and a reference nucleic acid is present in a greater amount in a sample comprising:

a) amplifying a target nucleic acid and a reference nucleic acid by polymerase chain reaction using a forward primer and a reverse primer for the target nucleic acid and a forward primer and a reverse primer for the reference nucleic acid, wherein the reverse primer for the reference nucleic acid comprises a tail sequence at its 5'-end which is identical to a portion of the target nucleic acid sequence;

b) adding a first disruption sequence which is complementary to the reverse primer for the target nucleic acid, and adding a second disruption sequence which is complementary to a portion, but not the tail sequence, of the reverse primer for the reference nucleic acid;

c) performing one or more PCR cycles, such that products of the PCR include single-stranded copies of the target nucleic acid and single-stranded copies of the reference nucleic acid that incorporate the complement of the tail sequence;

d) allowing the complement of the tail sequence to anneal with its complementary sequence on the target nucleic acid to yield a partially double-stranded nucleic acid molecule, a portion of which is extended to a double-stranded nucleic acid product, while any excess target nucleic acid or reference nucleic acid remains single-stranded;

e) crosslinking double-stranded nucleic acid in the mixture resulting from step (d); and f) detecting the presence of single-stranded target nucleic acid and reference nucleic acid, wherein the presence of a substantially greater amount of single-stranded target nucleic acid indicates that a greater amount of target nucleic acid was present in the sample, and the presence of a substantially greater amount of single-stranded reference nucleic acid indicates that a greater amount of reference nucleic acid was present in the sample.

2. The method of claim 1, wherein the double-stranded nucleic acid in step (e) comprises a halogenated nucleotide.

3. The method of claim 1, wherein crosslinking is performed using ultraviolet light.

4. The method of claim 1, wherein crosslinking is performed using a chemical crosslinker selected from the group consisting of mitomycin, carzinophilin, bizelesin, nitrogen mustard, netropsin, and derivatives thereof.

5. The method of claim 1, wherein the step of detecting is performed using a polymerase chain reaction.

6. The method of claim 1, wherein the step of detecting is performed using fluorescence, capillary electrophoresis, radioactivity, or enzyme activity.

7. The method of claim 1, wherein the sample is a biological sample.

8. The method of claim 7 wherein the biological sample is selected from the group consisting of blood, serum, plasma, a biopsy specimen, a swab, a smear, cell culture, RNA, and cDNA.

9. The method of claim 1, wherein the sample is not a biological sample.

10. The method of claim 7, wherein the sample is obtained from a pregnant woman.

11. The method of claim 10, wherein the target nucleic acid or the reference nucleic acid is a nucleic acid from a fetus.

12. The method of claim 11, wherein a difference between the amount of target nucleic acid and reference nucleic acid is related to a chromosomal abnormality in the fetus.

13. The method of claim 12, wherein the difference is related to Down syndrome in the fetus.

14. The method of claim 12, wherein the difference is related to Turner syndrome, Edwards syndrome, Patau syndrome, Klinefelter syndrome, Triple-X syndrome, or XYY syndrome in the fetus.

15. The method of claim 1, wherein a difference between the amount of target nucleic acid and reference nucleic acid is related to cancer.

* * * * *

UNITED STATES PATENT AND TRADEMARK OFFICE
CERTIFICATE OF CORRECTION

| | |
|---|---|
| PATENT NO. | : 8,642,264 B2 |
| APPLICATION NO. | : 11/909557 |
| DATED | : February 4, 2014 |
| INVENTOR(S) | : Szasz |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1726 days.

Signed and Sealed this
Fourteenth Day of April, 2015

Michelle K. Lee
*Director of the United States Patent and Trademark Office*

SEQUENCE LISTING

<160> NUMBER OF SEQ ID NOS: 11

<210> SEQ ID NO 1
<211> LENGTH: 20
<212> TYPE: DNA
<213> ORGANISM: Homo sapiens

<400> SEQUENCE: 1
gtatcactga taaaggagaa                                                    20

<210> SEQ ID NO 2
<211> LENGTH: 120
<212> TYPE: DNA
<213> ORGANISM: Homo sapiens

<400> SEQUENCE: 2
gaggagacca ggggctcaag tgagcccctc cgaggggatg gctgtgctgc agcagagata        60
tgactagaga caaccctcct gggccgactg ctagagaaca gcagcgccac tgttgcgtct       120

<210> SEQ ID NO 3
<211> LENGTH: 82
<212> TYPE: DNA
<213> ORGANISM: Homo sapiens

<400> SEQUENCE: 3
acaagctgca agctcacgac ttaccattcc gtaacgcttt tatgggctct gatgaccgag        60
gtctcaatgt cgattgggtg gt                                                82

<210> SEQ ID NO 4
<211> LENGTH: 20
<212> TYPE: DNA
<213> ORGANISM: Artificial
<220> FEATURE:
<223> OTHER INFORMATION: PCR Primer

<400> SEQUENCE: 4
gaggagacca ggggctcaag                                                    20

<210> SEQ ID NO 5
<211> LENGTH: 20
<212> TYPE: DNA
<213> ORGANISM: Artificial
<220> FEATURE:
<223> OTHER INFORMATION: PCR primer

<400> SEQUENCE: 5
agacgcaaca gtggcgctgc                                                    20

<210> SEQ ID NO 6
<211> LENGTH: 20
<212> TYPE: DNA
<213> ORGANISM: Artificial
<220> FEATURE:
<223> OTHER INFORMATION: PCR primer

<400> SEQUENCE: 6
agacgcaaca gtggcgctgc                                                    20

<210> SEQ ID NO 7
<211> LENGTH: 20
<212> TYPE: DNA
<213> ORGANISM: Artificial
<220> FEATURE:

```
<223> OTHER INFORMATION: PCR primer

<400> SEQUENCE: 7
gggccgactg ctagagaaca                                              20

<210> SEQ ID NO 8
<211> LENGTH: 20
<212> TYPE: DNA
<213> ORGANISM: Artificial
<220> FEATURE:
<223> OTHER INFORMATION: Complement of PCR primer

<400> SEQUENCE: 8
gcagcgccac tgttgcgtct                                              20

<210> SEQ ID NO 9
<211> LENGTH: 20
<212> TYPE: DNA
<213> ORGANISM: Artificial
<220> FEATURE:
<223> OTHER INFORMATION: Complement of PCR primer

<400> SEQUENCE: 9
ctcaatgtcg attgggtggt                                              20

<210> SEQ ID NO 10
<211> LENGTH: 20
<212> TYPE: DNA
<213> ORGANISM: Artificial
<220> FEATURE:
<223> OTHER INFORMATION: PCR primer

<400> SEQUENCE: 10
aggagggttg tctctagtca                                              20

<210> SEQ ID NO 11
<211> LENGTH: 20
<212> TYPE: DNA
<213> ORGANISM: Artificial
<220> FEATURE:
<223> OTHER INFORMATION: PCR primer

<400> SEQUENCE: 11
gggccgactg ctagagaaca                                              20
```